US012727917B2

(12) United States Patent
Wigginton et al.

(10) Patent No.: US 12,727,917 B2
(45) Date of Patent: Sep. 8, 2026

(54) ORTHOPEDIC EXTERNAL FIXATOR PIN CLAMP

(71) Applicant: New Standard Device, LLC, San Antonio, TX (US)

(72) Inventors: Robert E. Wigginton, McKinney, TX (US); Thomas L. Hand, San Antonio, TX (US); Ravi A. Karia, San Antonio, TX (US); Pedro Sandoval, San Antonio, TX (US)

(73) Assignee: New Standard Device, LLC, San Antonio, TX (US)

( * ) Notice: Subject to any disclaimer, the term of this patent is extended or adjusted under 35 U.S.C. 154(b) by 0 days.

(21) Appl. No.: 19/057,491

(22) Filed: Feb. 19, 2025

(65) Prior Publication Data

US 2026/0090827 A1 Apr. 2, 2026

Related U.S. Application Data

(62) Division of application No. 18/904,584, filed on Oct. 2, 2024, now abandoned.

(51) Int. Cl.
*A61B 17/64* (2006.01)
*A61B 17/00* (2006.01)

(52) U.S. Cl.
CPC ...... *A61B 17/6416* (2013.01); *A61B 17/6458* (2013.01); *A61B 2017/0042* (2013.01)

(58) Field of Classification Search
CPC ............ A61B 17/6416; A61B 17/6466; A61B 17/6458; A61B 17/645; A61B 17/6475; A61B 17/6483; F16B 2/04; F16B 2/06; F16B 2/12; F16L 3/1075; F16L 3/1083; F16L 3/1091; F16L 23/04
See application file for complete search history.

(56) References Cited

U.S. PATENT DOCUMENTS 6,652,523 B1 * 11/2003 Evrard .............. A61B 17/6466 606/56
2002/0042613 A1 * 4/2002 Mata .................. A61B 17/6466 606/59
2002/0077629 A1 * 6/2002 Hoffman ............ A61B 17/6466 606/59
2005/0261680 A1 * 11/2005 Draper .............. A61B 17/6425 606/59
2007/0038217 A1 * 2/2007 Brown .............. A61B 17/6466 606/57
2007/0161984 A1 * 7/2007 Cresina ............. A61B 17/6425 606/54
2012/0289959 A1 * 11/2012 Miller ................ A61B 17/6466 606/59
2017/0042579 A1 * 2/2017 Mannanal .......... A61B 17/6416
2017/0281236 A1 * 10/2017 Mussolin ........... A61B 17/6466
2019/0110815 A1 * 4/2019 Perret ................ A61B 17/6466

* cited by examiner

*Primary Examiner* — Julianna N Harvey

(57) ABSTRACT

An orthopedic clamp for use in conjunction with an external bone fixation (EBF) device, comprising an upper clamp, comprising an upper portion of a pin channel; a lower clamp, comprising a lower portion of the pin channel; a flexible hinge coupled between the upper clamp and lower clamp; and a shaft hole that passes through the upper and lower clamps, configured to accept a bolt for attachment of the orthopedic clamp to an orthopedic strut.

15 Claims, 9 Drawing Sheets

ORTHOPEDIC EXTERNAL FIXATOR PIN CLAMP

REFERENCE TO RELATED APPLICATION

This application is a Divisional of and claims priority to U.S. patent application Ser. No. 18/904,584, filed on Oct. 2, 2024, the contents of which are incorporated herein by reference in its entirety.

FIELD OF THE DISCLOSURE

The claimed subject matter relates generally to a clamp for an orthopedic strut and, more specifically, a modular clamp that can attach an orthopedic pin to an orthopedic strut used in orthopedic external fixation devices.

BACKGROUND

External Bone Fixation (EBF) devices are employed in the treatment of bone deformity and acute trauma. Typical EBF devices use plates in which adjustable connection rods and struts are employed to connect the plates together. Current connection rods have only a conical range of seven degrees (7°) and struts have only forty-seven degrees (47°), which reduces the functionality of the rods and struts, limiting the possible configurations for connecting the plates together. Half pins and wires are employed to attach the plates to a patient's bone to stabilize the bone while the bone or bones are being corrected or healing. The half pins and wires attach to the EBF device at one or two points and are either drilled into or through a bone.

One well-known reconstructive EBF system is the Ilizarov frame, as shown in U.S. Pat. Nos. 4,365,624; 4,615,338; 4,978,348; 5,702,389 and 5,971,984. The Ilizarov frame uses a combination of circular frames, pins and wires for deformity correction.

SUMMARY

Provided is a clamp for attaching a telescoping, adjustable strut that connects plates employed in orthopedic external bone fixation (EBF) devices to pins and wires that secure the EBF to a patient's bones. The disclosed clamp is especially useful in trauma situations where speed and adjustment are essential. The telescoping, adjustable struts incorporate the disclosed clamp and lockable swivel hinges. The swivel hinges provide one hundred eighty degrees (180°) of movement in one direction and three hundred sixty degrees (360°) of rotation in another direction. A lockable swivel hinge is typically positioned on each end of a telescoping, adjustable strut. EBF devices, which employ the telescoping, adjustable struts and clamp, are used to fix broken bones and to stabilize bones that are being corrected or healing.

An orthopedic clamp for use in conjunction with an external bone fixation (EBF) device, comprising an upper clamp, comprising an upper portion of a pin channel; a lower clamp, comprising a lower portion of the pin channel; a flexible hinge coupled between the upper clamp and lower clamp; and a shaft hole that passes through the upper and lower clamps, configured to accept a bolt for attachment of the orthopedic clamp to an orthopedic strut. In addition, the disclosed clamp is modular in that it can convert an orthopedic strut from a plate-to-plate application, a plate-to-pin application and a pin-to-pin application.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures.

DETAILED DESCRIPTION OF THE FIGURES

The illustrations and diagrams in the Figures illustrate the architecture, functionality, and operation of possible implementations of systems according to various embodiments of the present invention.

Figure 1:
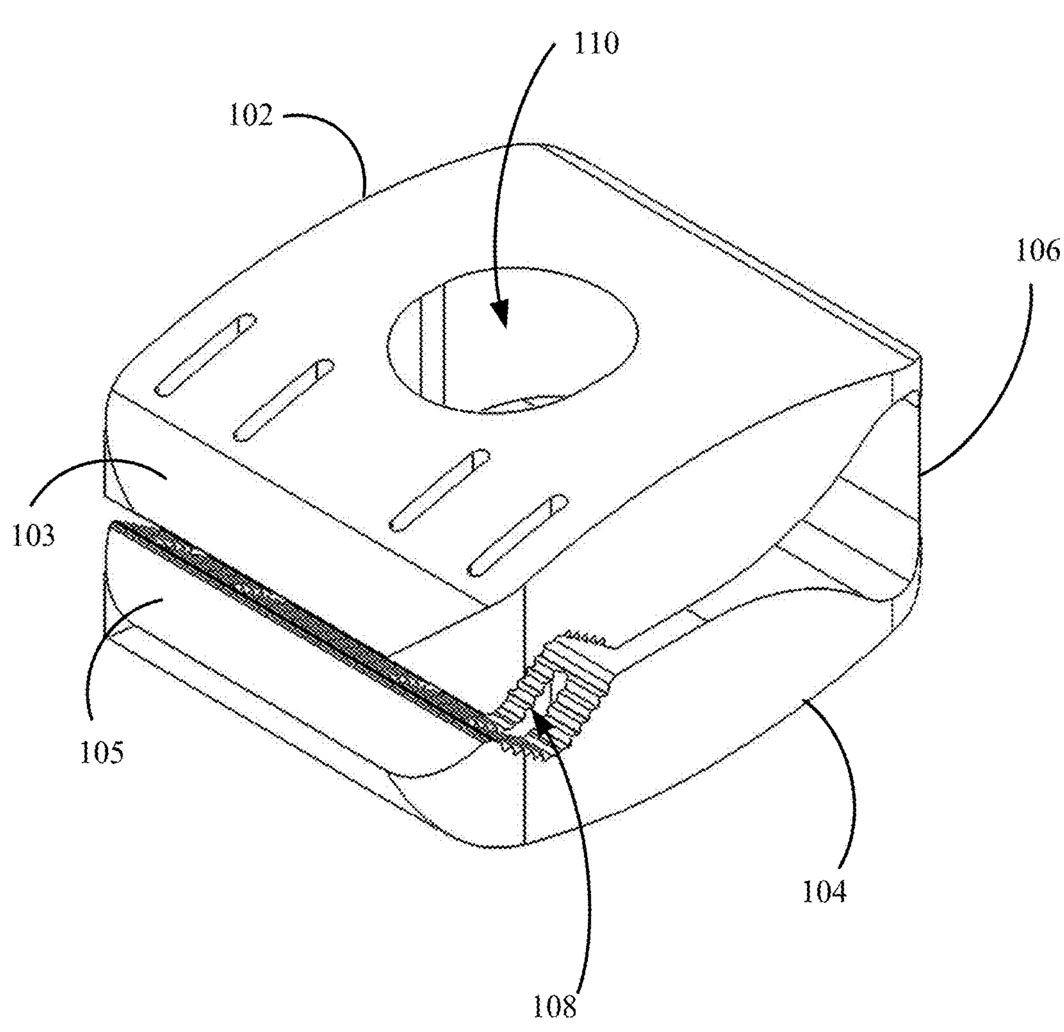
FIG. 1 is an illustration of one embodiment of Orthopedic Fixator Pin Clamp (OFPC) in accordance with the claimed subject matter

Turning now to the figures, FIG. 1 is an illustration of one embodiment of an Orthopedic Fixator Pin Clamp (OFPC) 100 in accordance with the claimed subject matter. OFPC includes an upper clamp 102 and a lower clamp 104. Upper clamp 102 and lower clamp 104 are coupled together by a hinge 106. Hinge 106 is constructed of a flexible material that enables the distance between front edges 103 and 105 of clamps 102 and 104, respectively, to be slightly separated so that an orthopedic pin (see 162, FIGS. 4 and 5) may be positioned in a pin channel 108. A shaft hole 110 enables OFPC 100 to be secured to an orthopedic strut (see 150, FIG. 3-6). Pin channel 108 and shaft hole 110 are explained in more detail below in conjunction with FIGS. 3 and 4.

Figure 2:
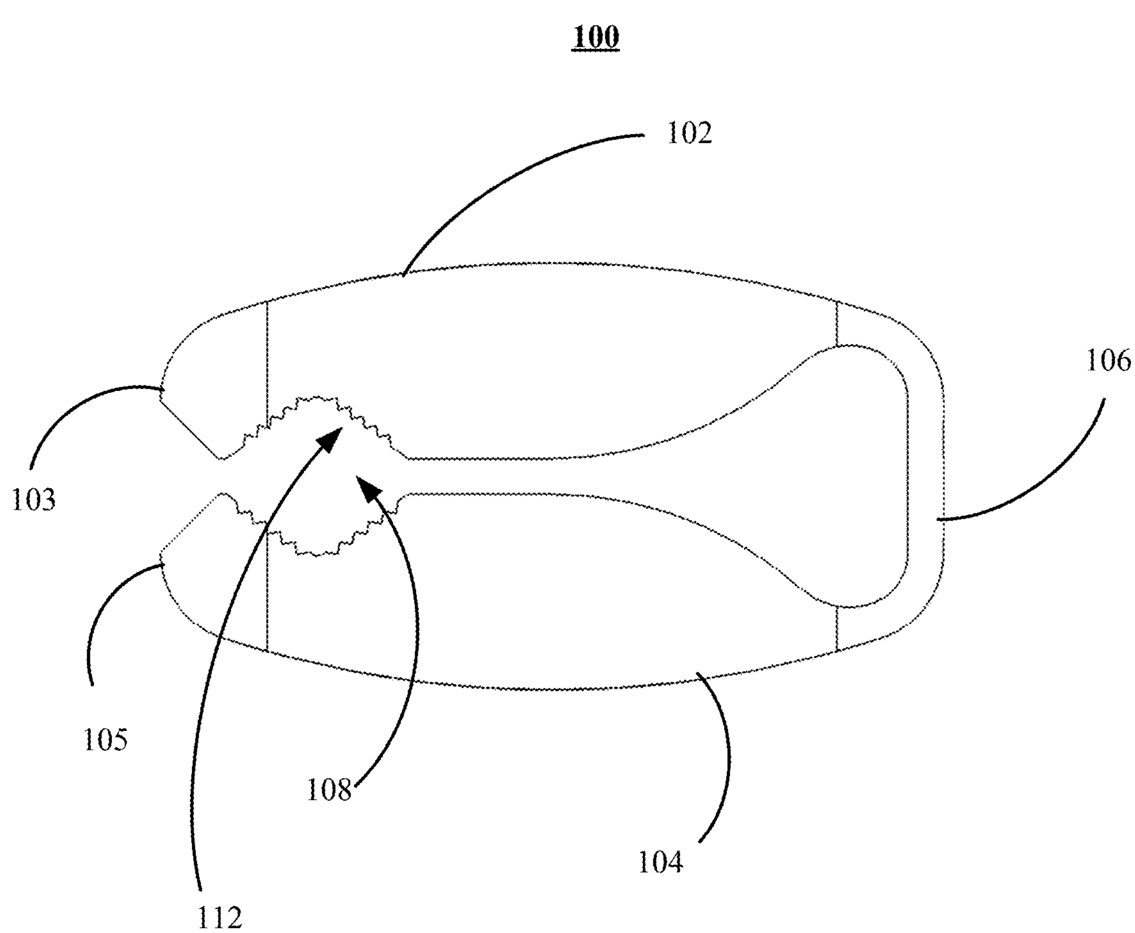
FIG. 2 is an illustration of the OFPC of FIG. 1 from a different perspective.

FIG. 2 is an illustration of OFPC 100 of FIG. 1 from a different perspective, showing upper clamp 102, edge 103, lower clamp 104, edge 105, hinge 106 and pin channel 108. Also Illustrated in FIG. 2 are pin grip ridges 112 on an inner surface of upper and lower clamps 102 and 104 within pin channel 108. Pin grip ridges 112 run along the length of pin channel 108 and serve to provide a more secure grip on a pin (see 162, FIGS. 4 and 5).

Figure 3:
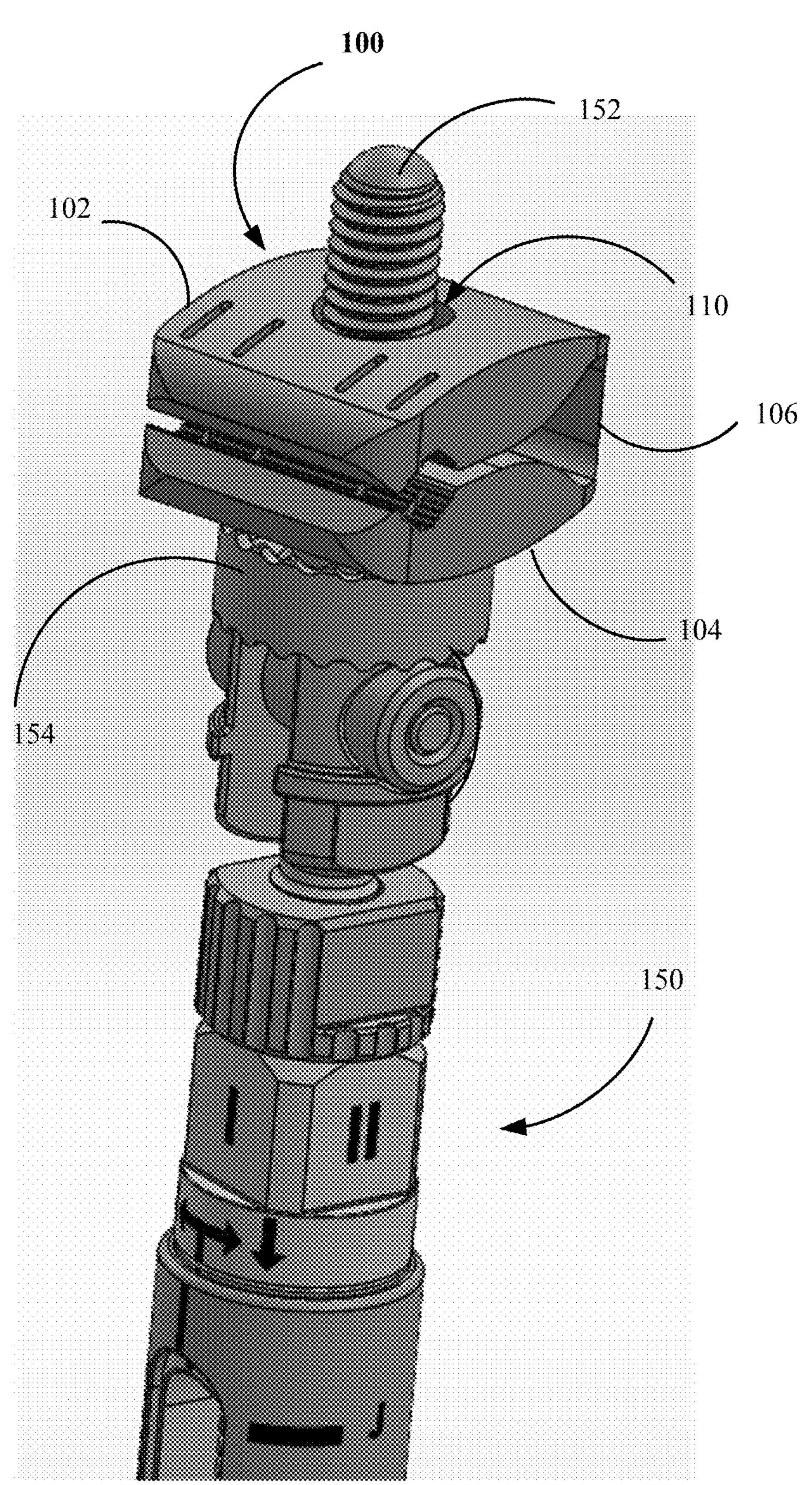
FIG. 3 is an illustration of the OFPC of FIGS. 1 and 2 mounted on a telescoping, adjustable strut.

FIG. 3 is an illustration of the OFPC 100 of FIGS. 1 and 2 mounted on, but not secured to, a telescoping, adjustable orthopedic strut 150. Like in FIGS. 1 and 2, FIG. 3 also shows upper clamp 102, lower clamp 104, hinge 106 and shaft hole 110 of OFPC 100. A strut attachment stud, or bolt, 152 of strut 150 is illustrated inserted through shaft hole 110. In addition, multiple OFPCs 100 may be stacked (see FIG. 9) on strut attachment bolt 152 to provide attachment points for multiple pins (see 162, FIG. 4).

Strut 150 includes a serrated collar 154 that is positioned against a lower surface of OFPC 100 and is configured to prevent OFPC 100 from rotating around strut attachment bolt 152 when OFPC 100 is secured to strut 150.

Figure 4:
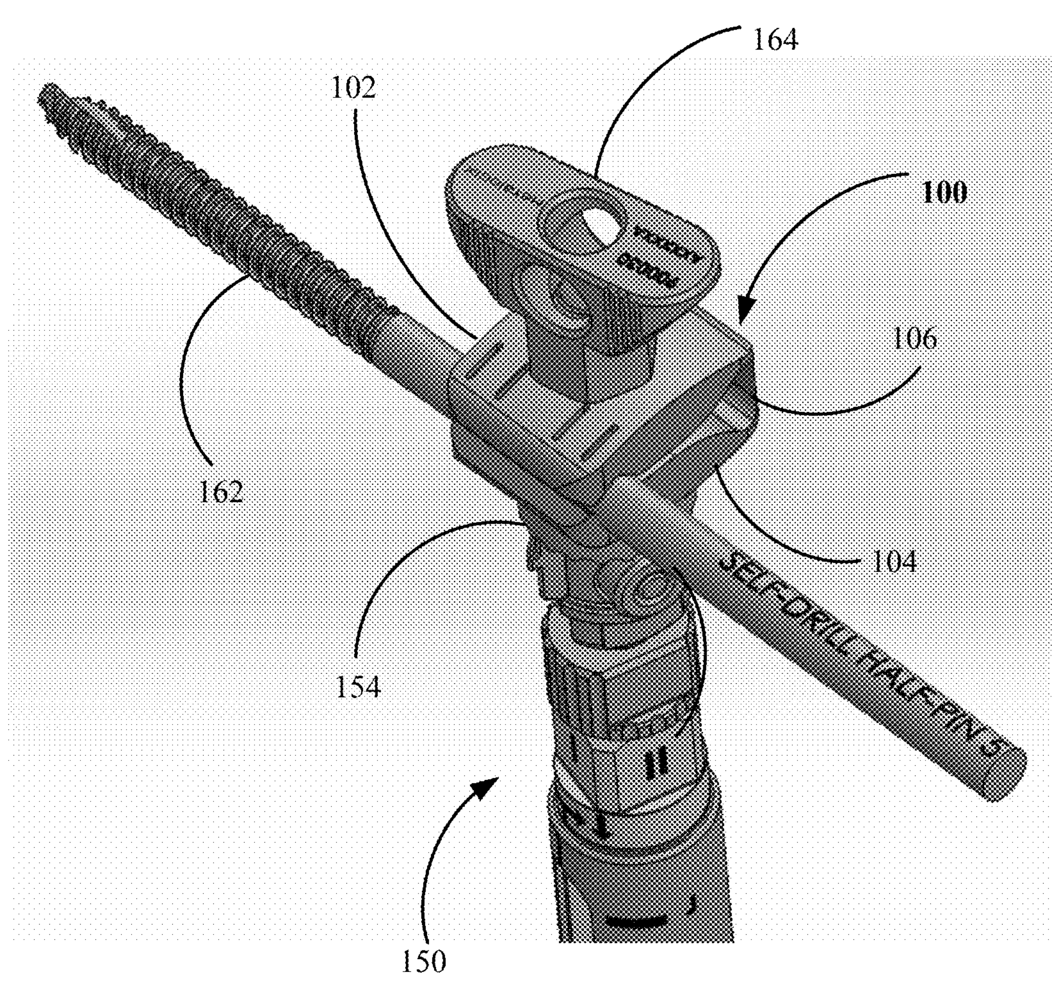
FIG. 4 is an illustration of the OFPC of FIGS. 1-3 installed and secured on the telescoping, adjustable strut of FIG. 3 and securing a pin.

FIG. 4 is an illustration of the OFPC 100 of FIGS. 1-3 installed and secured on telescoping, adjustable strut 150 of FIG. 3. OFPC 100 includes upper clamp 102, lower clamp 104 and hinge 106. An orthopedic pin 162 is inserted through pin channel 108 (FIGS. 1 and 2). Orthopedic pin 162 may be, but is not limited to, various diameters with four millimeter, five millimeter and six millimeter (4 mm, 5 mm and 6 mm) being most common. It should be understood that practically any size pin may be accommodated, for example eighteen millimeter (18 mm). Flexible hinge 106 enables orthopedic pin 162 to be "snapped" into pin channel 108 by providing enough flexibility for upper clamp 102 and lower clamp 104 to be slightly separated with enough clearance for pin 162 and then forced back together to provide some grip on pin 162. A strut attachment nut 164 is screwed onto strut attachment bolt 152 (FIG. 3) thereby securing OFPC 100 more tightly to strut 150. The tightening of strut attachment nut 154 also forces upper clamp 102 and lower clamp 104 together to secure pin 162 in pin channel 108. The tightening of strut attachment nut 164 also pushes serrated collar 154 against OFPC 100 to prevent any rotation of OFPC 100 with respect to strut 150.

Figure 5:
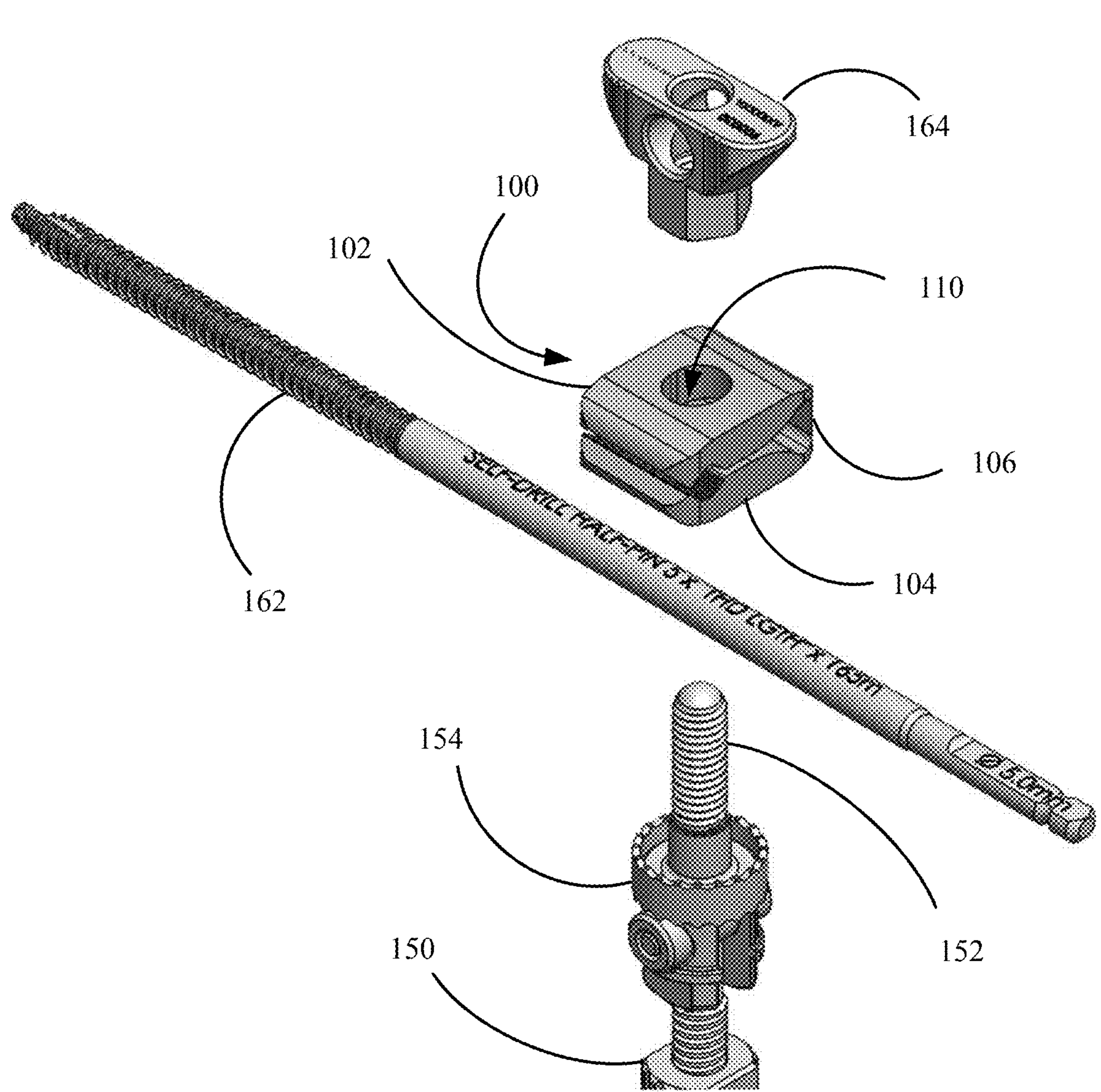
FIG. 5 is an illustration of the OFPC of FIGS. 1-4 disasembled.

FIG. 5 is an illustration of the OFPC 100 of FIGS. 1-4 and strut 150 of FIGS. 3 and 4 dissembled. As in previous figures, upper clamp 102, lower clamp 104, hinge 106, strut 150, strut attachment bolt 152, serrated collar 154, orthopedic pin 162 and strut attachment bolt 164 are shown.

Figure 6:
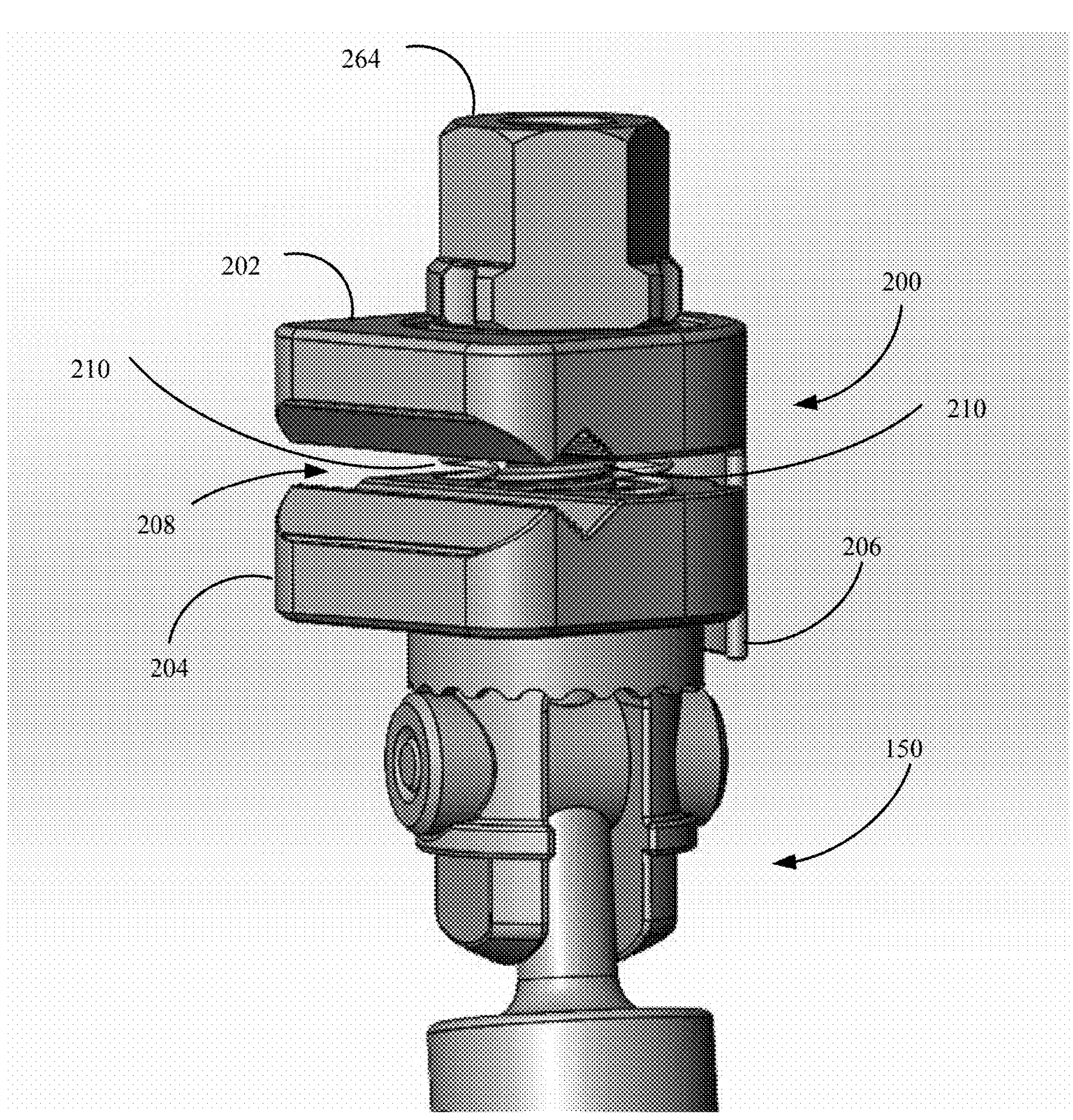
FIG. 6 is an illustration of an alternative embodiment 200 of an OFPC.

FIG. 6 is an illustration of an alternative embodiment of an OFPC 200 mounted on strut 150 (FIGS. 4-6). Like OFPC 100 of FIGS. 1-5, OFPC 200 includes an upper clamp 202 and a lower clamp 204. Rather than hinge 106 (FIGS. 1-5), upper clamp 202 and lower clamp 204 are coupled with a lip 206 on upper clamp 202 that enables a gap between clamps 202 and 204 to be adjusted. A pair of springs 210 pull upper clamp 202 and lower clamp 204 together so that a pin such as orthopedic pin 162 (FIGS. 4 and 5) may be snapped into place in a pin channel 208. In an alternative embodiment, a single spring centered around a shaft hole (not shown) may be employed rather than springs 210.

Figure 7:
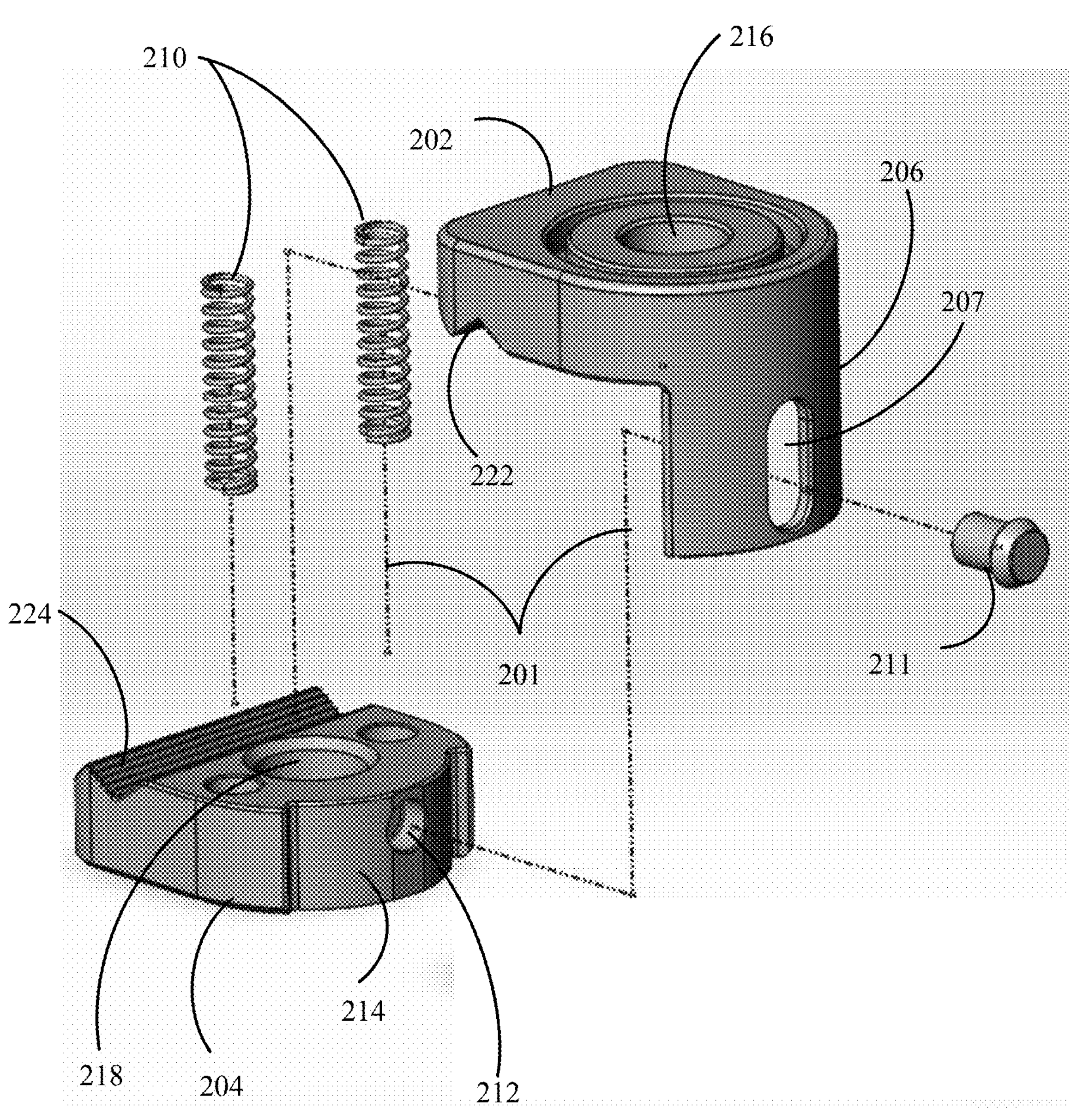
FIG. 7 is an illustration of an alternative embodiment 300 of an OFPC.

FIG. 7 is a view of OFPC 200 of FIG. 6 disassembled so that the various components are clearly visible. Dotted lines such as dotted lines 201 are used to indicate how particular components fit together. Like OFPC 100 of FIGS. 1-5, OFPC 200 includes upper clamp 202 and lower clamp 204. Upper clamp 202 has lip 206 with a slot 207. A bolt 211 is inserted through slot 207 in lip 206, screwing into a threaded hole 212 in lower clamp 204. In this manner, upper clamp 202 and lower clamp 204 may be secured with respect to each other. In addition, lip 206 is configured to fit into an indentation 214 in lower clamp 204 that prevents upper clamp 202 from rotating with respect to lower clamp 204. A shaft hole 216 through upper clamp 202 corresponds to and lines up with a shaft hole 218 in lower clamp 204. OFPC 200 includes two springs 210 coupled in between upper and lower clamps 202 and 204. Springs 210 are configured to pull upper and lower clamps 202 and 204 together so that an orthopedic pin (see 162, FIGS. 4 and 5) may be snapped into place and temporarily secured before nut 164 (see FIG. 5) is tightened. Pin 162 fits into an upper pin channel 222 in upper clamp 202 that corresponds and runs parallel to a lower pin channel 224 in lower clamp 204.

Figure 8:
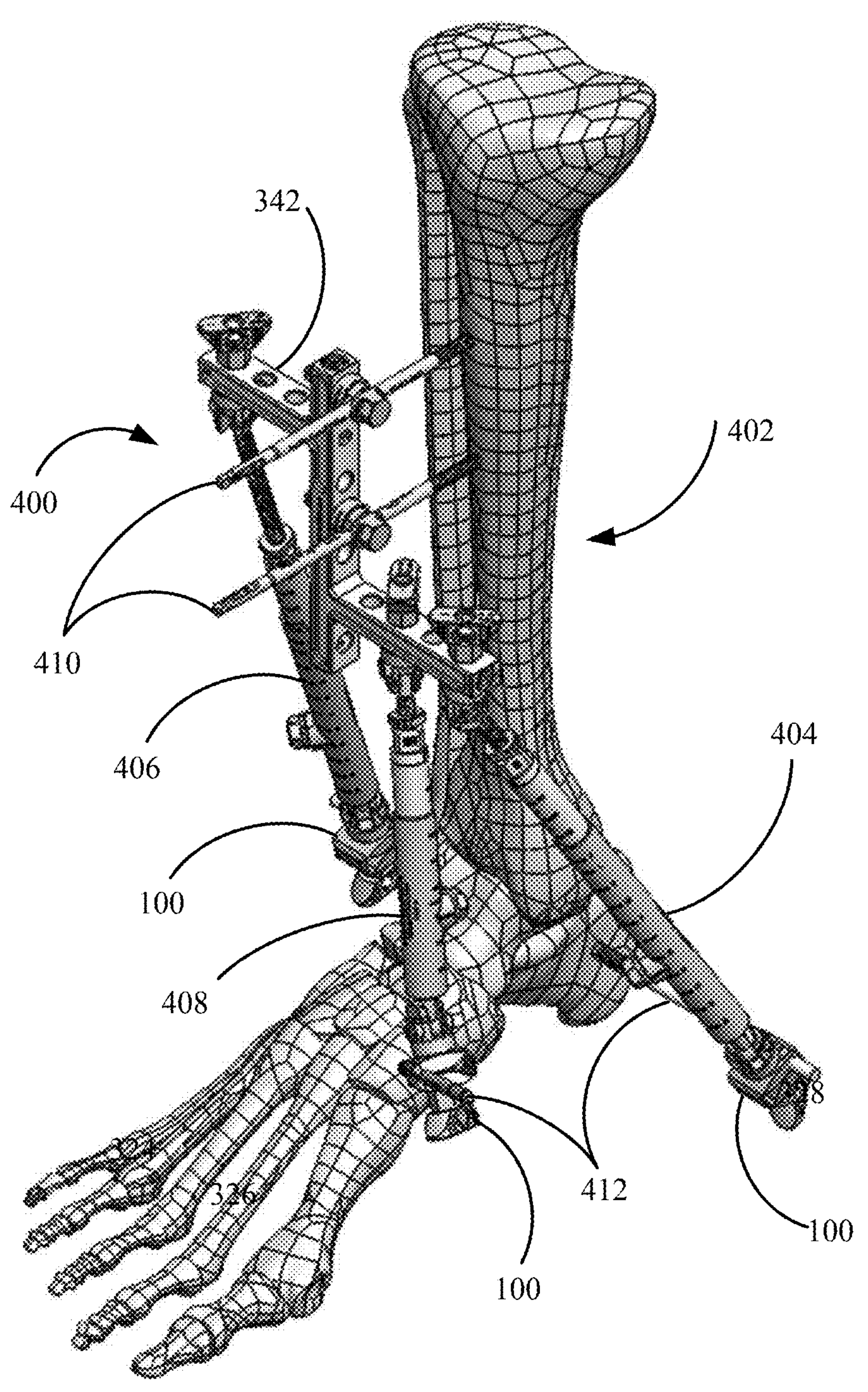
FIG. 8 is an illustration of OFPC of FIGS. 1-5 employed in conjunction with an orthopedic External Fixation Device (EFD).

FIG. 8 is an illustration of OFPC 100 of FIGS. 1-5 employed in conjunction with a with an orthopedic External Fixation Device (EFD) 400. EFD 400 is shown installed on a patient's leg and foot bones 402 and includes three (3) telescoping adjustable struts 404, 406 and 408. Struts 404, 406 and 408 are each attached to a Z plate 342 that is attached to patient's leg bone 402 by means of pins 410. Each of struts 404, 406 and 408 have a OFPC 100 at the lower end. Orthopedic pins 412 are held in place by OFPCs 100 at the end of struts 404 and 408. It should be understood that in addition to the application illustrated in FIG. 8 the disclosed technology is equally applicable to enable a strut to be utilized in orthopedic plate-to plate, plate-to-pin and pin-to-pin applications.

Figure 9:
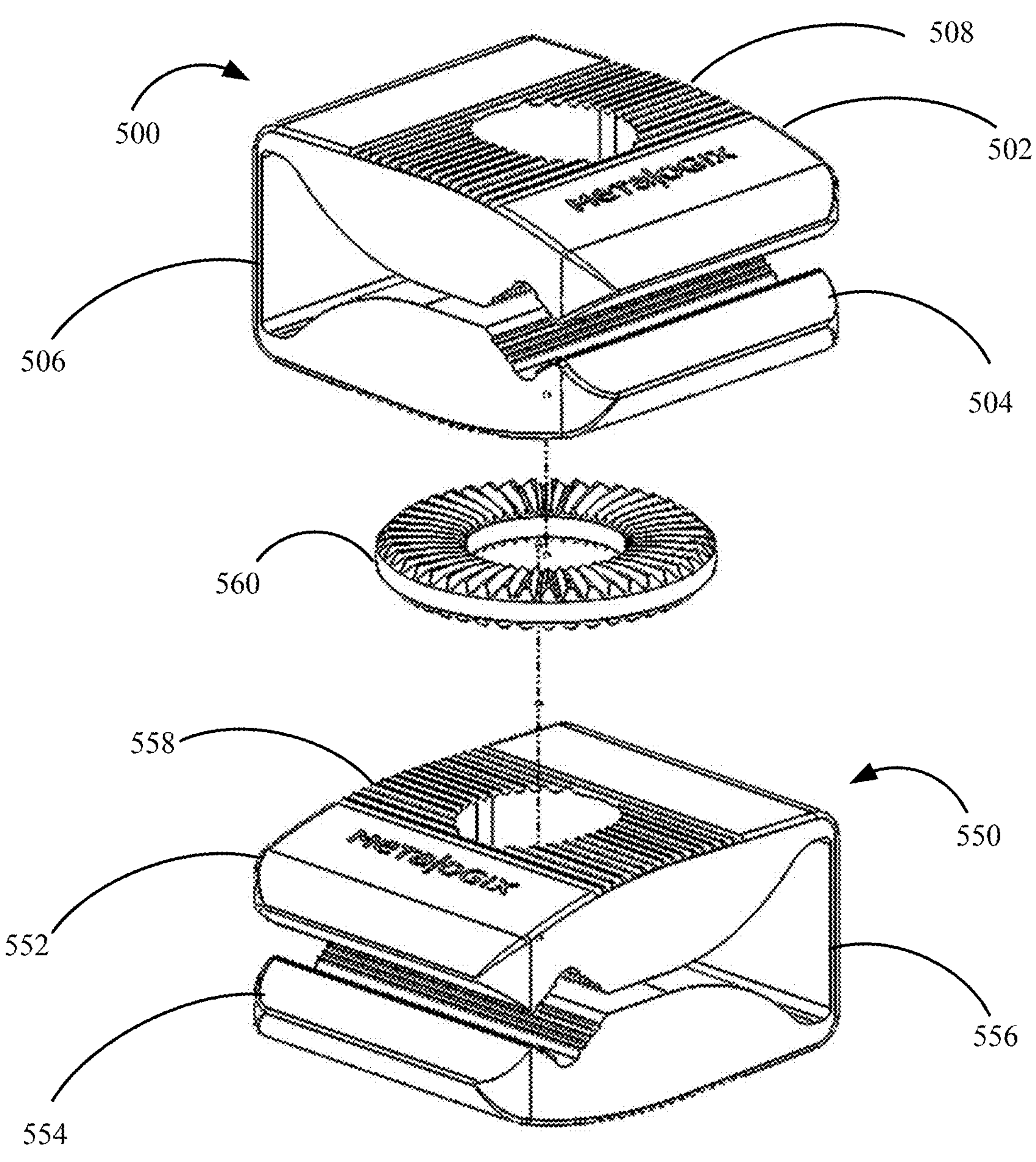
FIG. 9 is an illustration of a pair of OFPCs adapted to be employed in a stacked configuration.

FIG. 9 is an illustration of a pair of OFPCs 500 and 550 adapted to be employed in a stacked configuration. OFPC 500 includes an upper clamp, or "jaw," 502, a lower jaw 504 and a hinge 506. OFPC 550 includes an upper jaw 552, a lower jaw 554 and a hinge 556. OFPC 500 also includes a series of parallel anti-rotation ridges 508 on an outer surface, i.e., the surface not on the side of a pin channel. of upper jaw 502. Although not visible in FIG. 9, anti-rotation ridges, such as anti-rotation ridges 506 may also be on an outer surface of lower jaw 504. In a similar fashion, OFPC 550 includes anti-rotation ridges 558 and may include anti-rotation rides on a lower surface. Also included in FIG. 9, is an anti-rotation washer 560 that is adapted to fit between OFPCs 500 and 550. Although not illustrated it should be understood that OFPCs 500 and 550 are adapted to fit onto, i.e. be stacked on, a strut attachment bolt, such as strut attachment bolt 152 (FIG. 3).

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements.

What is claimed is:

1. An orthopedic clamp for use in conjunction with an external bone fixation (EBF) device, comprising:
- an upper clamp comprising:
- an upper portion of a pin channel;
- a single lip extending from the upper clamp comprising an oblong slot; and
- a first hole through the upper clamp parallel to the lip;
- a circular groove surrounding the first hole;
- a first spring hole and a second spring hole; and
- a lower clamp, comprising;
- a lower portion of a pin channel;
- a second channel configured to accommodate the lip such that the lip fits within the second channel;
- a second hole through the lower clamp, wherein the first and second holes are in alignment when the lip is within the second channel;
- a pin hole through the lower clamp, wherein the pin hole and the oblong slot are configured to align when the lip is within the second channel;
- a third spring hole and a fourth spring hole; and
- a pin that passes through the oblong slot into the pin hole and couples to the lower clamp; and
- a a first spring coupled to the upper clamp within the first spring hole;
- a second spring coupled to the upper clamp within the second spring hole;

the first spring coupled to the lower clamp within the third spring hole;

the second spring coupled to the lower clamp within the fourth spring hole; and wherein the first spring and the second spring are configured to pull the upper clamp and the lower clamp together.

2. The orthopedic clamp of claim 1, wherein the second channel is configured to prevent rotation of the upper clamp relative to the lower clamp.

3. The orthopedic clamp of claim 1, wherein the first spring and the second spring are placed on opposing sides of the first hole and the second hole.

4. The orthopedic clamp of claim 1, wherein the first spring and the second spring are adapted to enable a pin to be inserted into the pin channel.

5. The orthopedic clamp of claim 1, further comprising a nut, a bolt, and a pin, wherein a nut screwed onto a bolt inserted through the first and second holes forces the upper clamp and lower clamp together, thereby securing a pin in the pin channel, wherein:

the bolt is configured to be inserted through the first hole and the second hole;

the nut is configured to be screwed onto the bolt;

the nut and bolt are configured to apply force to the upper clamp and the lower clamp, thereby securing the pin within the pin channel.

6. The orthopedic clamp of claim 1, wherein the orthopedic clamp is adapted to enable an orthopedic strut to be utilized in plate-to-pin and pin-to-pin applications.

7. The orthopedic clamp of claim 1, the upper and lower portions of the pin channel comprising pin grip ridges.

8. An orthopedic strut for use in conjunction with an external bone fixation (EBF) device, comprising:

a telescoping orthopedic strut; and a plurality of orthopedic clamps coupled to the orthopedic strut, each orthopedic clamp comprising:

an upper clamp comprising:

an upper portion of a pin channel;

a single lip extending from the upper clamp comprising an oblong slot; and a first hole through the upper clamp parallel to the lip;

a circular groove surrounding the first hole;

a first spring hole and a second spring hole; and a lower clamp, comprising;

a lower portion of a pin channel;

a second channel configured to accommodate the lip such that the lip fits within the second channel;

a second hole through the lower clamp, wherein the first and second holes are in alignment when the lip is within the second channel;

a pin hole through the lower clamp, wherein the pin hole and the oblong slot are configured to align when the lip is within the second channel;

a third spring hole and a fourth spring hole; and a pin that passes through the oblong slot into the pin hole and couples to the lower clamp;

a first spring and a second spring coupled to the upper clamp and the lower clamp configured to pull the upper clamp and the lower clamp together; and the first hole and the second hole are configured to accept a bolt for attachment of the orthopedic clamp to the orthopedic strut.

9. The orthopedic strut of claim 8, wherein the lip is configured to fit into the second channel to prevent rotation of the upper clamp relative to the lower clamp.

10. The orthopedic strut of claim 8, wherein the first spring and the second spring are placed on opposing sides of the first hole and the second hole.

11. The orthopedic strut of claim 8, wherein the the first spring and the second spring are adapted to enable an orthopedic pin to be snapped into place in the pin channel.

12. The orthopedic strut of claim 8, further comprising a nut, a bolt, and a pin, wherein a nut screwed onto a bolt inserted through the first and second holes forces the upper clamp and lower clamp together, thereby securing a pin in the pin channel. wherein:

the bolt is configured to be inserted through the first hole and the second hole;

the nut is configured to be screwed onto the bolt;

the nut and bolt are configured to apply force to the upper clamp and the lower clamp, thereby securing the pin within the pin channel.

13. The orthopedic strut of claim 8, wherein the orthopedic clamp is adapted to enable the orthopedic strut to be utilized in plate-to-pin and pin-to-pin applications.

14. The orthopedic strut of claim 8, wherein the upper and lower portions of the pin channel comprise pin grip ridges.

15. The orthopedic strut of claim 8, further comprising a serrated collar abutting the orthopedic clamp and configured to prevent the rotation of the lower clamp relative to the bolt.

* * * * *